United States Patent [19]

Meischen et al.

[11] 4,284,579
[45] Aug. 18, 1981

[54] (N-PHOSPHONACETYL-L-ASPARTATO)(1,2-DIAMINOCYCLCHEXANE)PLATINUM(II) OR ALKALI METAL SALT

[75] Inventors: Sandra J. Meischen; Glen R. Gale, both of Charleston, S.C.; Marion B. Naff, Bethesda, Md.

[73] Assignee: The United States of America as represented by the of the Department of Health & Human Services, Washington, D.C.

[21] Appl. No.: 155,531

[22] Filed: Jun. 9, 1980

Related U.S. Application Data

[63] Continuation-in-part of Ser. No. 58,287, Jul. 17, 1979, abandoned.

[51] Int. Cl.$^3$ .............................................. C07F 15/00
[52] U.S. Cl. ............................... 260/429 R; 424/166; 424/287
[58] Field of Search ................. 260/429 R; 424/287, 424/166

[56] References Cited

U.S. PATENT DOCUMENTS

| | | | |
|---|---|---|---|
| 4,115,418 | 9/1978 | Gale et al. | 260/429 R |
| 4,137,248 | 1/1979 | Gale et al. | 260/429 R |
| 4,140,707 | 2/1979 | Cleare et al. | 260/429 R |
| 4,169,846 | 10/1979 | Kidani et al. | 260/429 R |

OTHER PUBLICATIONS

Meischen et al., J. Natl. Cancer Inst., 57 (4), pp. 841–845, 1976.
Schwartz et al., Cancer Treatment Reports, vol. 61, No. 8, pp. 1519–1525, (1977).

*Primary Examiner*—Helen M. S. Sneed
*Attorney, Agent, or Firm*—John S. Roberts, Jr.

[57] ABSTRACT

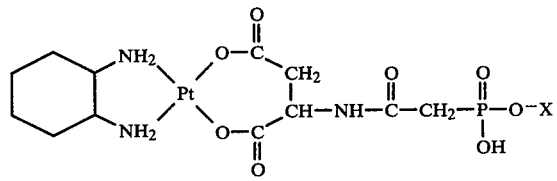

where X is Na$^+$, K$^+$, Li$^+$ or H (N-phosphonacetyl-L-aspartato)(1,2-diaminocyclohexane)platinum(II) or alkali metal salt thereof has shown antitumor activity in animals such as activity against murine leukemia L1210. Additionally, this agent is used against B-16 and Colon 38 tumors and also Ehrlich ascites tumor. It is effective in dosages of 5–60 mg/kg of body weight and is potentiated in a treatment with cyclophosphamide (CY) (50 mg/kg of body weight) to which may be added hydroxyurea (HU) (1000–1500 mg/kg of body weight).

In binary treatment with cis-dichlorodiamine-platinum-(II) (or cisplatin) the preferred ratio of the present compound to cisplatin is about 10:1 with a range of about 10:1 to 1:10 in mg/kg of body weight.

As to the variations in the formula on the left hand side of the formula, it may be varied as monodentate, such as cisplatin containing a single amine group proceeding from the ring, or bidentate, such as the present compound. The saturated cyclo ring may be C$_4$ or C$_5$–C$_7$ in addition to the present cyclohexane.

The present platinum compound may be prepared by reacting the known L-aspartic acid, N-(phosphonacetyl-) disodium salt (PALA; NSC-224131), with dinitrato(1,2-diaminocyclohexane)platinum(II) (NSC-239851). This compound N-phosphonacetyl-L-aspartato(1,2-diaminocyclohexane)platinum(II) may be combined in multiple drug regimen with substantially improved yield cures over the parent compounds. For example, the compound denoted Pt-268 may be combined in a dual regimen with cyclophosphamide (CY), hydroxyurea (HU), and cisplatin.

2 Claims, 4 Drawing Figures

(N-PHOSPHONACETYL-L-ASPARTATO)(1,2-DIAMINOCYCLCHEXANE)PLATINUM(II) OR ALKALI METAL SALT

This is a continuation-in-part of pending application Ser. No. 058,287 filed July 17, 1979, now abandoned.

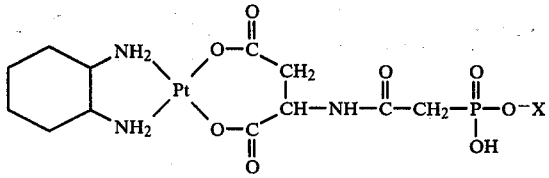

where X is Na+, K+, Li+, or H (N-phosphonacetyl-L-aspartato)(1,2-diaminocyclohexane)platinum(II) or alkali metal salt thereof has shown antitumor activity in animals such as activity against murine leukemia L1210. Additionally, this agent is used against B-16 and Colon 38 tumors and also Ehrlich ascites tumor. It is effective in dosages of 5-60 mg/kg of body weight and is potentiated in a treatment with cyclophosphamide (CY) (50 mg/kg of body weight) to which may be added hydroxyurea (HU) (1000-1500 mg/kg of body weight).

In binary treatment with cis-dichlorodiamineplatinum(II) (or cisplatin) the preferred ratio of the present compound to cisplatin is about 10:1 with a range of about 10:1 to 1:10 in mg/kg of body weight.

As to the variations in the formula on the left hand side, it may be varied as monodentate, such as cisplatin containing a single amine group proceeding from the ring, or bidentate, such as the present compound. The saturated cyclo ring may be $C_4$ or $C_5$-$C_7$ in addition to the present cyclohexane.

As examplary of alternative structures, if the nitrogen (or other) donor ligand is designated as A or B, and the N-phosphonacetyl-L-aspartate as PALA, coordinated via the two anionic carboxyl oxygen atoms, the following general structure is obtained:

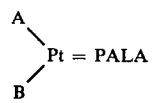

[=indicates chelation to N-(phosphonacetyl)-disodium salt, or PALA; NSC-224131]
where A and B are monodentate (A-, B-) or bidentate (AB-) amine (or other donor atoms/groups) compounds binding to platinum.

Specific examples include:
Bidentate aliphatic:

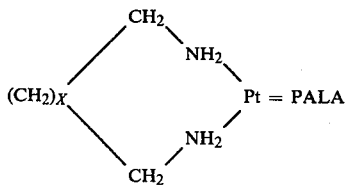

where X=0, 1, or >1 and the carbon chain may contain 0, 1, or >1 double bonds.
Monodentate aliphatic:

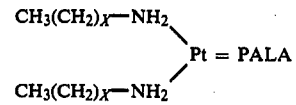

where X=0, 1, or >1; where the N atom is either normal (n; straight chain) or iso to the aliphatic moiety; and the chain may contain 0, 1, or >1 double bonds.
Bidentate alicyclic:

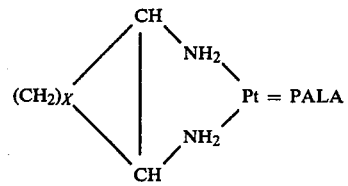

where X=1, or >1 and the ring may contain 1 or >1 double bonds; specifically, where X=4 and the ring is saturated, the subject matter of the present invention is described by the formula (NSC-314926; Pt-268).
Monodentate alicyclic:

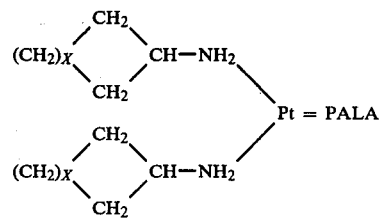

where X=0, 1, or >1 and double bonds may be present in the rings.
Bidentate aromatic:

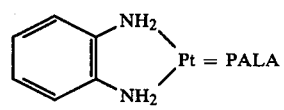

where the aromatic

may be substituted or unsubstituted.
Monodentate aromatic:

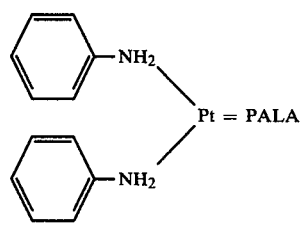

where the aromatic

may be substituted or unsubstituted.
Heterocyclic:

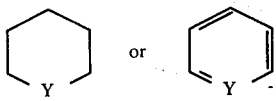

where Y=N, O, or S or any other donor atom.
Inorganic (Ammine):

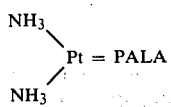

The present platinum compound may be prepared by reacting the known L-aspartic acid, N-(phosphonacetyl-) disodium salt (PALA; NSC-224131), with dinitrato (1,2-diaminocyclohexane)platinum(II) (NSC-239851). This compound N-phosphonacetyl-L-aspartato (1,2-diaminocyclohexane)platinum(II) may be combined in multiple drug regimen with substantially improved yield cures over the parent compounds. For example, the compound denoted Pt-268 may be combined in a dual regimen with cyclophosphamide (CY), hydroxyurea (HU), and cisplatin.

PRIOR ART STATEMENT

U.S. Pat. No. 4,115,418 Gale/Meischen
U.S. Pat. No. 4,137,248 Gale/Schwartz
Hill, et al, "Further Clinical Experience with cis-Platinum(II) Diamminedichloride," ed. Connors et al, *Platinum Coordination Complexes in Cancer Chemotherapy*, Springer-Verlag, New York, 1974, pages 145–152.

P. Schwartz et al, "Preparation for Antitumor Evaluation of Water-Soluble Derivatives of Dichloro(1,2-diaminocyclohexane)platinum(II)", *Cancer Treatment Reports*, November 1977, pages 1519–1525.

S. J. Meischen et al, "Antileukemic Properties of Organoplatinum Complexes," *J. Natl. Cancer Inst.*, Vol. 57, No. 4, October 1976, pages 841–845.

DEFINITIONS

It is noted that the NSC numbers in this application are the official numbers made public by the National Cancer Institute and the following numbers are particularly utilized.

| NSC-26271 | Cyclophosphamide |
| NSC-32065 | Hydroxyurea |
| NSC-119875 | Cis-dichlorodiamine-platinum(II) (cisplatin) |
| NSC-194814 | Dichloro(1,2-diaminocyclohexane)-platinum(II) |
| NSC-224131 | N-(phosphonacetyl-)disodium salt (PALA) |
| NSC-239851 | Dinitrato(1,2-diaminocyclohexane)-platinum(II) |
| NSC-314926 | N-phosphonacetyl-L-aspartato(1,2-diaminocyclohexane)platinum(II), Na (Pt-268) |
| NSC-328005 | N-phosphonacetyl-L-aspartato(1,2-diaminocyclohexane)platinum(II) (acid form) |

THE METHOD OF PROCEEDING

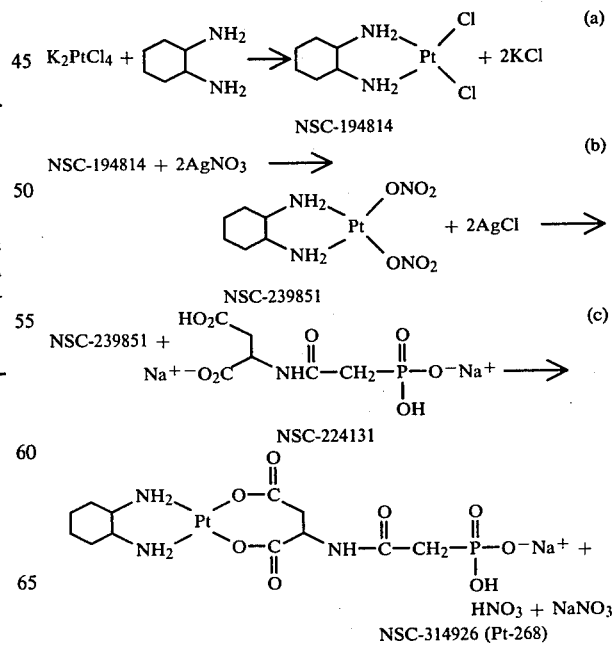

In the above schematic, step (a) recites the conventional preparation of cisplatin (NSC-194814) and in steps (b) and (c) 1.38 grams (4.6 mmoles) of PALA [N-(phosphonacetyl-)disodium salt] was added to 1.6 grams (3.7 mmoles) of dinitrato(1,2-diaminocyclohexane)platinum(II) (NSC-239851). These reactants were initially dissolved in a minimum of distilled water prior to mixing. The reaction mixture was stirred overnight at room temperature with a flow of filtered air to facilitate evaporation. The solid material was collected and dissolved in 20 ml of distilled water. To this solution was added 300 ml of ethanol; the solution was stirred at room temperature for 30 minutes, the reprecipitated cream-colored material (NSC-314926) was filtered from solution and dried in vacuo. The yield was 1.49 grams or 50% of theoretical yield.

As set out above in the prior art statement, cis-dichlorodiamine-platinum(II) (cisplatin) has been the subject of recent research developments.

Figure 3:
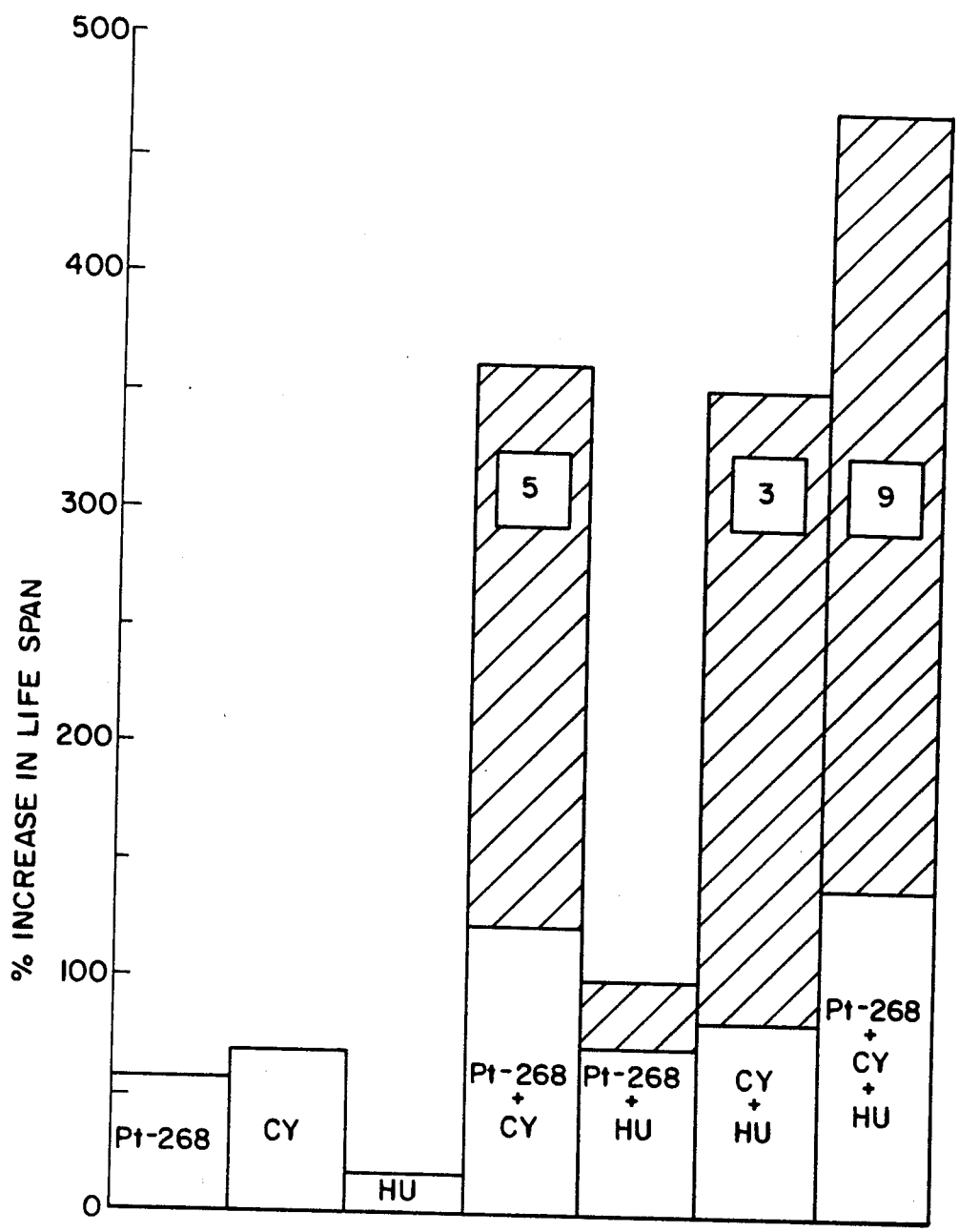
FIG. 3 shows the effect of Pt-268 when used in combination with cyclophosphamide and hydroxyurea on survival times of mice bearing advanced L1210 leukemia. Numbers superimposed on the bars = number of cures (>50-day survivors) in each group of 10 treated mice. Mice received $10^6$ L1210 cells intraperitoneally on Day 0. Each compound was given as a single intraperitoneal injection on Day 3.

The present compound has been tested alone and in combination with cyclophosphamide and hydroxyurea. It is believed that there is a substantial advantage synergistically in the combination of Pt-268 and cyclophosphamide although the advantage as with hydroxyurea was minimal. In the ternary system with Pt-268 plus cyclophosphamide plus hydroxyurea, there is a substantial synergistic advantage over the binary system with cyclophosphamide and the results of this multiple therapy are set out in FIG. 3.

As to the modus of action, the PALA group apparently dissociates or leaves from the Pt-268 complex rather slowly. For example, when Pt-268 is dissolved in 0.9% NaCl solution, displacement of the PALA with chlorides, as evidenced by the appearance of an insoluble precipitate of dichloro(1,2-diaminocyclohexane)-platinum(II) (NSC-194814), does not occur until about eight hours after dissolution. Therefore, it seems probable that the intact Pt-268 complex may be transported into or otherwise gain access into the tumor cell. Although the tumor cell of L1210 leukemia appears to resist PALA, attachment of PALA to the 1,2-diaminocyclohexane-platinum moiety in Pt-268 may afford a means of access into the cell of the inhibitor of aspartate transcarbamylase, which is an enzyme in de novo pyrimidine synthesis.

Figure 4:
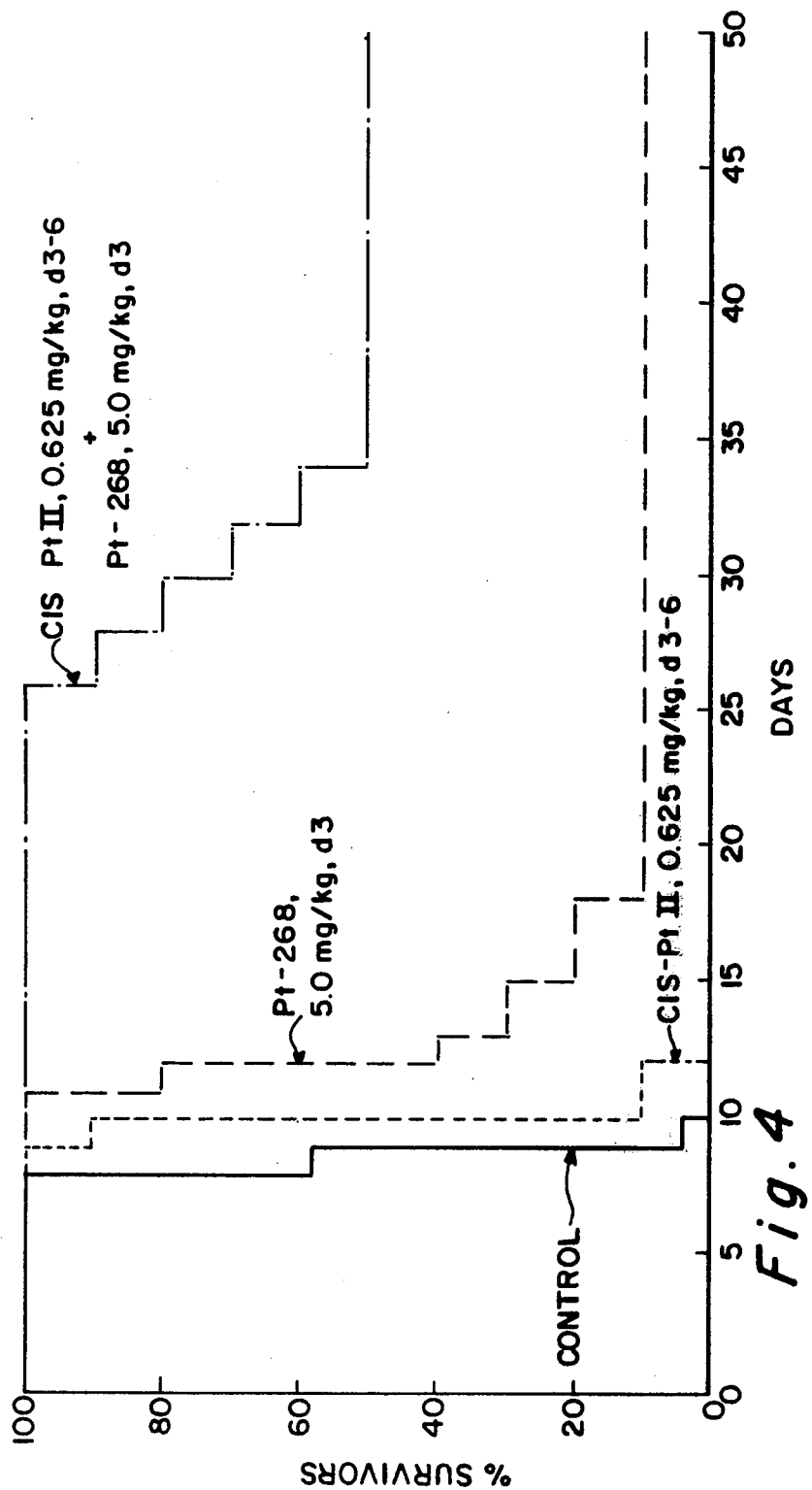
FIG. 4 shows the effect of Pt-268 when used in combination with cisplatin (NSC-119875). Mice were given an inoculum of $10^6$ L1210 cells. One group received Pt-268 on Day 3; another group received cisplatin on Days 3, 4, 5, and 6; and a third group received the two drugs in combination on the same schedule. This third group of animals showed an increased median life span of 25 days over the control group with a cure rate (>50-day survivors) of 50%.

In addition to the multiple drug regimen noted above, it has further been found that a synergistic relationship is achieved by the utilization of a binary drug combination of cisplatin (NSC-119875) and platinum-PALA (NSC-314926). A combination therapy involving these two and its efficacy is set out in FIG. 4. With reference to FIG. 4, BDF$_1$ mice were given an inoculum of $10^6$ L1210 cells. On Day 3, one group received NSC-314926, 5 mg/kg. Another group received NSC-119875, on Days 3, 4, 5, and 6 at a barely active dose of 0.625 mg/kg each day. Another group received the two drugs in combination on the same schedule. It is noted that despite the fact that low dosages of each of the drugs were hardly effective in increasing the median life span when the two drugs were given in combination, the increase in the median life span was 25 days over that of controls and the cure rate (>50-day survivors) was 50%.

EXAMPLE 1

Elemental analyses of N-phosphonacetyl-L-aspartato(1,2-diaminocyclohexane)platinum(II) (Pt-268; NSC-314926):

(Galbraith Laboratories, Knoxville, Tennessee)

|   | % Calculated (as anhydrous) | % Calculated (with 1.95% H$_2$O) | % Found |
|---|---|---|---|
| C | 24.66 | 24.18 | 24.04 |
| H | 3.62 | 3.77 | 3.99 |
| N | 7.19 | 7.05 | 7.01 |
| O | 21.90 | 23.22 | 25.46 |
| P | 5.30 | 5.20 | 5.29 |
| Pt | 33.38 | 32.72 | 30.51 |
| Na | 3.93 | 3.85 | 3.42 |

Karl Fisher analysis: 1.95% water
(Galbraith Laboratories, Knoxville, Tennessee)
Solubility:
Soluble in water to ~175 mg/ml
Soluble in CH$_3$Oh to ~0.2 mg/ml
One ml of each of the following solvents dissolved approximately 2 mg of Pt-268:
Formic acid
Glacial acetic acid
Ammonia A 2-mg sample was either very slightly soluble or insoluble in each of the following solvents:

| | |
|---|---|
| ethanol | dimethylformamide |
| acetone | dimethylsulfoxide |
| tetrahydrofuran | cyclopentanone |
| t-butanol | heptane |
| CHCl$_3$ | |

Thin layer chromatography:
Cellulose on polyethylene (Eastman 13255)
Solvent system. N-butanol/acetic acid/H$_2$O, 5/2/3
Reference. PALA
Detection.
  (1) SnCl$_2$ in 1.0 N HCl
  (2) Bromcresol green in 0.1% ethanol
  (3) 0.1% AgNO$_3$ with 2 N NH$_4$OH until precipitate dissolves
  (4) Ultraviolet absorption Results. The platinum-PALA complex was detected by all methods as a major spot with R$_f$ of 0.69, while PALA was identified as a major spot at R$_f$=0.41. A minor platinum-PALA component was faintly observed at R$_f$~0.54.

Ultraviolet (uv) spectrum:
The uv spectrum of platinum-PALA complex at $10^{-4}$ molar concentration has a prominent peak at 200 nm with a shoulder at 240 nm. The 200 nm peak decreases with time while the 240 nm peak becomes more prominent. The spectrum stabilizes within 10 hours. PALA also exhibits the characteristic end absorption with a peak at 278 nm in 1% aqueous solution.

EXAMPLE 2

Antineoplastic Activity

The N-phosphonacetyl-L-aspartato(1,2-diaminochclohexane)platinum(II) complex (Pt-268; NSC-314926) was dissolved in 5% glucose and tested for its activity in the L1210 leukemia in mice. LD$_{50}$ was determined in tumored BDF$_1$ mice and was found to be 180 mg/kg. The BDF$_1$ mice received $10^6$ L1210 leukemia cells by I.P. injection on Day 0 and were divided into groups of 10, including a control group of 40 mice. The treated groups were treated on Day 1 only at different dose levels from 10 mg/kg to 200 mg/kg or treated on Days 1, 5, and 9 at dose levels from 2.5 mg/kg to 50 mg/kg.

Figure 1:
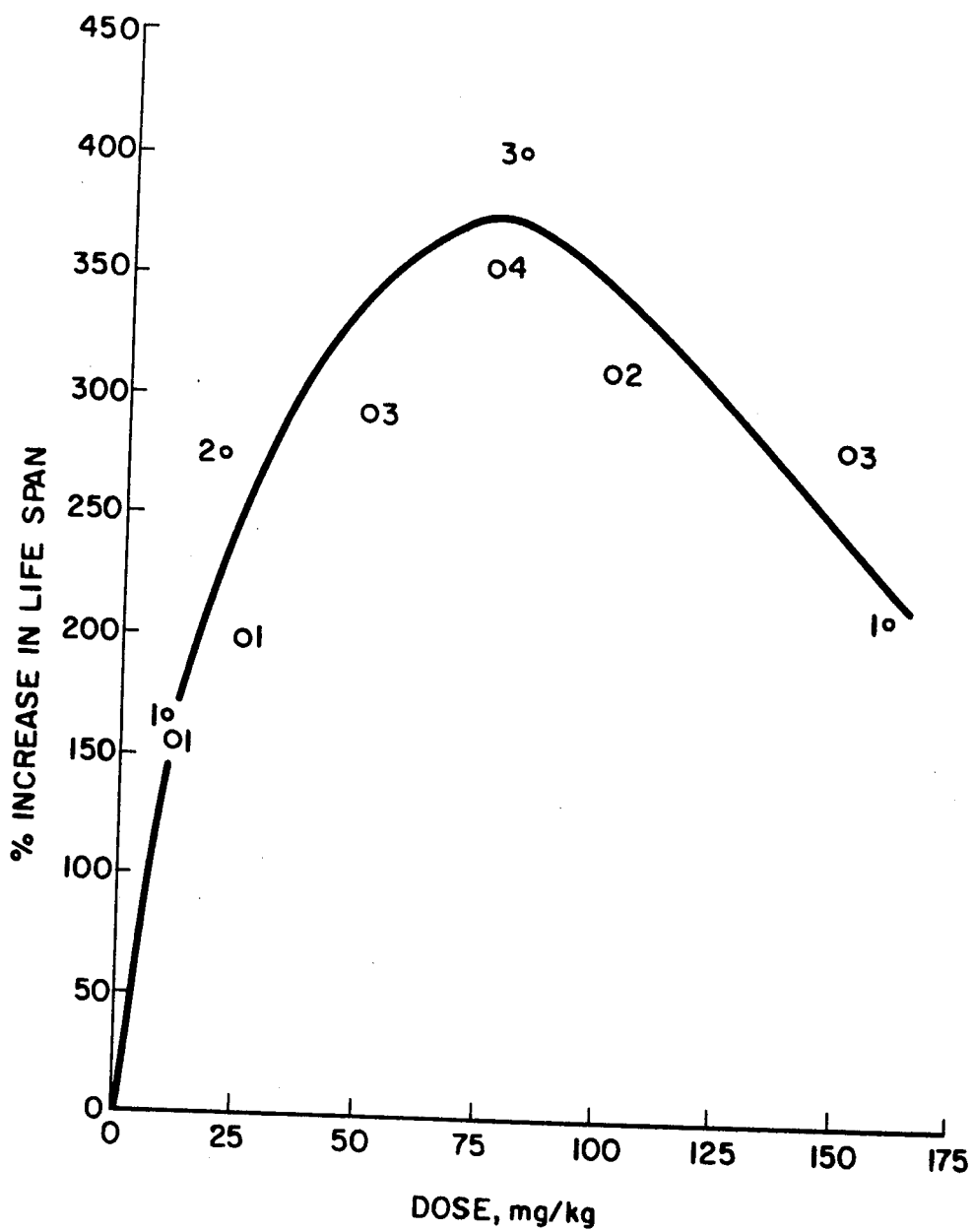
FIG. 1 shows the effect of N-phosphonacetyl-L-aspartato (1,2-diaminocyclohexane)platinum(II) [Pt-268] on life spans of mice bearing L1210 leukemia. Mice received $10^6$ L1210 cells on Day 0 via intraperitoneal route. Pt-268 was given intraperitoneally on Day 1 only in 5% glucose solution. Numbers adjacent to symbols = number of >60-day survivors in each group of 10 mice. Control survival times = 203 hours.

FIG. 1 shows the dose-response curve for Day 1 only treatment. The optimal therapeutic dose for this schedule was approximately 80 mg/kg. Defining a therapeutic safety ratio as the I.P. dose required to kill 50% of the animals ($LD_{50}$) compared to the I.P. dose which is 50% of the optimal therapeutic dose ($LD_{50}/OptD_{50}$), one obtains a value of 4.5 for the above complex as compared to the therapeutic safety ratio of 2.7 for cisplatin when calculated by the same method ($LD_{50}=17$ mg/kg I.P.; Opt $D_{50}=6.25$ mg/kg I.P.)

Figure 2:
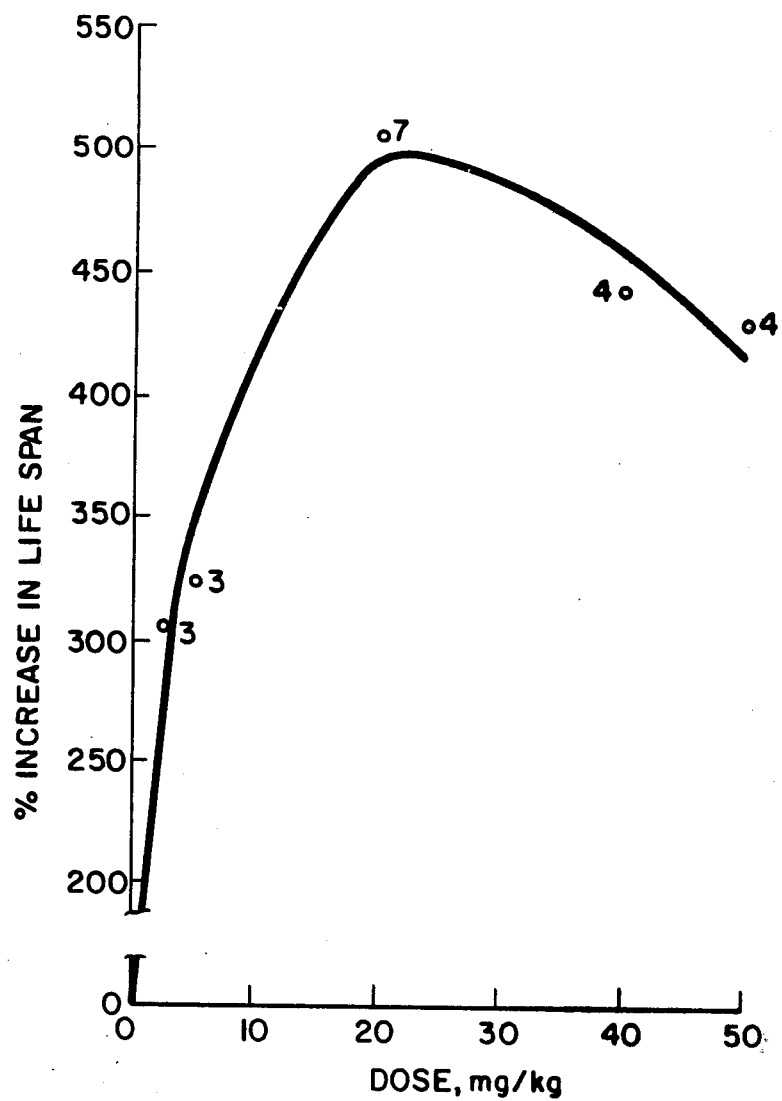
FIG. 2 shows the effect of Pt-268 on life spans of mice bearing L1210 leukemia. Mice received $10^6$ L1210 cells on Day 0 via intraperitoneal route. Pt-268 was given intraperitoneally on Days 1, 5, and 9 in 5% glucose solution. Numbers adjacent to symbols = number of >60-day survivors in each group of 10 animals. Control survival time = 203 hours.

FIG. 2 summarizes the results obtained from a dose schedule in which Pt-268 was administered on Days 1, 5, and 9. The optimal dose in this study was approximately 20 mg/kg when given at this regimen.

A further study was carried out to assess any additive or synergistic effect with cyclophosphamide (NSC-26271) and hydroxyurea (NSC-32065). The platinum-PALA complex, which is the present compound (Pt-268) was used at a dose of 5.0 mg/kg I.P., cyclophosphamide was used at 40–50 mg/kg I.P., and hydroxyurea at 1000 mg/kg I.P. The treatments tested were (1) the three agents used alone, (2) each agent used in combination with each of the other two agents, and (3) all three agents used together. The results indicate Pt-268 exhibits a synergistic effect with cyclophosphamide in the dual combination as well as the triple combination with hydroxyurea.

In addition to testing with L1210 leukemia, satisfactory responses against tests by additional animal cancer organisms have been shown as, for example, Ehrlich ascites tumor, melanoma B-16 and Colon 38. Testing was achieved using either the alkali metal (sodium) salt or the free acid.

EXAMPLE 3

Protocol for B-16 and Colon 38 Tumors

B-16. Essentially this was a procedure for mice where the tumor was at least 400 mg in size. Median control survival time was 14–22 days for I.P. tumor. A reproduced T/C≧125% was considered worthy of further study.

Colon 38. The protocol is similar to that of the previous cancer and the drug treatment was I.P. on Days 2 and 9.

EXAMPLE 4

NSC-328005, the Free Acid Form

The N-phosphonacetyl-L-aspartate (PALA; NSC-224131) as received from the National Cancer Institute had a purity of 87±2% and consisted of 64% disodium salt and 26% trisodium salt. The remainder was water and ethanol. Therefore, the stoichiometry was adjusted so that 2.5 grams (8.36 mmoles) of the PALA would be added to 3.55 grams (8.2 moles) of dinitrato(1,3-diaminocyclohexane)platinum(II) (NSC-239851). Initially the reactants were dissolved in deionized water; PALA in 25 ml, and NSC-239851 in 300 ml with warming in the latter instance to promote dissolution. To the PALA solution was added 50 ml wet volume of Dowex 50W-X4 resin to remove $Na^+$ from PALA:

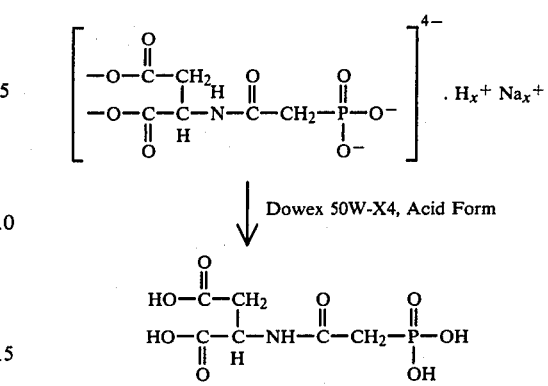

To remove nitrate from NSC-239851, a 25 ml wet volume of Dowex 1-8X which had been pretreated with 10 N NaOH to remove chloride ion and replace it with hydroxide ion was added to the NSC-239851 solution:

The synthesis of NSC-268252 is described in Schwartz et al., Cancer Treatment Report, 61:1519-1525, 1977. The solutions were allowed to react with the resins and were then filtered from the resins, combined, and the mixture was transferred to the flask of a vacuum flask evaporator. Upon removal of all the water, the product was dissolved in 30 ml of water, filtered, and 400 ml of absolute ethanol was added to precipitate the white product. Yield of NSC-328005 was approximately 30% of the theoretical value.

The final reaction can be depicted thus:

NSC-328005 can also be used as the starting material for producing the alkali metal salt form. This is done by titrating with a known amount of alkali metal base such as sodium bicarbonate.

EXAMPLE 5

Effects of N-phosphonacetyl-L-aspartato(1,2-diaminocyclohexane)platinum on the Ehrlich ascites tumor The chart below shows survival times of BDF$_1$ mice bearing the Ehrlich ascites carcinoma. Mice received an intraperitoneal inoculation of 10$^7$ tumor cells on Day 0; treatment was by the intraperitoneal route on Day 1 only. NSC-314926 [N-phosphonacetyl-L-aspartato(1,2-diaminocyclohexane)platinum(II)] was dissolved in 5% dextrose solution. There were 10 mice per group.

| Dose, mg/kg | Survival Time Days | T/C × 100* |
|---|---|---|
| 0 | 13.4 | — |
| 5 | 16.5 | 123 |
| 10 | 18.8 | 140 |
| 20 | 24.3 | 181 |
| 40 | 25.3 | 189 |
| 60 | 28.8 | 215 |
| 80 | 29.0 | 216 |
| 100 | 31.7 | 237 |

*T/C = treated group survival time/control survival time

Claims:
1. The compound (N-phosphonacetyl-L-aspartato)(1,2-diaminocyclohexane)platinum(II) or alkali metal salt of the formula

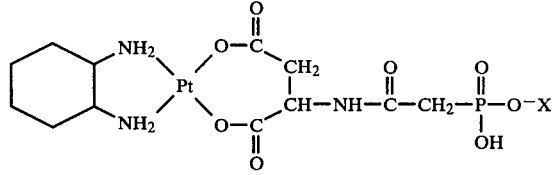

where X is Na$^+$, K$^+$, Li$^+$, or H

2. The compound of claim 1 wherein the alkali metal salt is sodium salt.

* * * * *